A cold stable liquid reagent system suitable for use in a Jaffe method for the determination of creatinine comprises:
United States Patent [19]

Seaton

[11] Patent Number: 4,950,611
[45] Date of Patent: Aug. 21, 1990

[54] COLD STABLE LIQUID CREATININE REAGENT

[75] Inventor: Charles B. Seaton, San Diego, Calif.

[73] Assignee: Beckman Instruments, Brea, Calif.

[21] Appl. No.: 67,365

[22] Filed: Jun. 26, 1987

[51] Int. Cl.⁵ ............................................. G01N 33/70
[52] U.S. Cl. ........................................................ 436/98
[58] Field of Search ............................................ 436/98

[56] References Cited

FOREIGN PATENT DOCUMENTS

WO88/10429 12/1988 PCT Int'l Appl. .

*Primary Examiner*—Robert J. Warden
*Assistant Examiner*—David Redding
*Attorney, Agent, or Firm*—Michael B. Farber

[57] ABSTRACT

A cold stable liquid reagent system suitable for use in a Jaffe method for the determination of creatinine comprises:
(a) a homogeneous liquid picric acid component comprising picric acid in an amount of no more than about 35 mM, such that the picric acid component remains visibly homogeneous at a temperature between about 2 to about 8° C. for 30 days or more;
(b) a homogeneous liquid alkaline buffer component comprising:
  (i) an alkaline material in sufficient amount to maintain the pH of the alkaline buffer component at more than about 13, for controlling the pH of the assay ready reagent formed by combining the picric acid and alkaline buffer components;
  (ii) at least one pH buffer material;
  (iii) a detergent for reducing interference by proteins in the Jaffe method; and
  (iv) borate for reducing interference by carbohydrates in the Jaffe method;

wherein the alkaline buffer components contains substantially no metallic cations such that the component remains visibly homogeneous at a temperature between about 2° to about 8° C. for 30 days or more. Preferably the alkaline material is tetramethylammonium hydroxide, and the detergent is diethanolamine dodecyl sulfate.

10 Claims, 9 Drawing Sheets

COLD STABLE LIQUID CREATININE REAGENT

BACKGROUND

This invention is directed to a reagent system for the determination of creatinine.

Creatinine, 1-methylglycocyamidine, $C_4H_7ON_3$, is the end product of creatinine metabolism. It is one of the non-protein constituents of blood. Creatinine is a normal alkaline constituent of urine and blood. In humans, about 0.02 gm/kg. of body weight is excreted by the kidneys per day. Increased quantities of creatinine in the body fluids is generally an indication of renal malfunction.

There are several different methods for body fluid creatinine determination. Most of these methods are based on the picrate reaction with creatinine under alkaline conditions, as described by Jaffe M. Jaffe, Z. Physiol., Chem., 10(1886)391. The creatinine-picrate complex absorbs strongly at 520 nm, and its presence can be measured calorimetrically. The concentration of creatinine can thus be determined either by measuring the final absorbance at 520 nm, or by measuring the rate of change of absorbance at 520 nm. The latter is known as the rate Jaffe method.

A number of substances in body fluids are known to interfere with the Jaffe reaction, and increase the color yield. These substances include, for example, glucose, proteins, acetoacetate and pyruvate. Therefore, the Jaffe reaction suffers from lack of specificity. Attempts have been made to separate the creatinine from the interfering substances, proteins, carbohydrates, etc.), such as by means of ion exchange chromatography. But this method is time consuming, requires highly skilled operators, and is not suitable for routine analysis of a large number of samples.

The current practice is to use borates, and organic sulfates, to eliminate non-specific color formation due to interference by the reaction of chromogen-forming substances (other than creatinine) with picrate in alkaline conditions. This method enables creatinine determination without prior deproteinization. For example, proteins combine with sodium dodecyl sulfate (SDS) to form very stable complexes with a large number of negatively charged sulfate groups. Borates form negatively charged complexes with carbohydrates under alkaline conditions. Carbohydrates are neutral. One explanation of the efficacy of SDS and borate is that the negatively charged complexes and the picrate ions repel each other and are thus prevented from reacting. In this way nonspecific color formation in the Jaffe reaction can be reduced. Also, the presence of SDS allows the preparation of a reaction mixture blank, since acidification to eliminate the creatinine color does not precipitate the negative SDS-protein complexes. This allows the measurement of the blank absorbance. It was reported that the results obtained by using the SDS-borate reagents correlate well with those obtained with a method involving isolation of creatinine with a chromatographic procedure.

The pH of the reaction mixture also affects the color developed. The higher the pH, the faster the rate of color formation, and the stronger the final color. Current practice is to incorporate a pH buffer, such as a phosphate buffer, in the alkaline SDS-borate reagent This maintains the pH within a predetermined narrow range, such as a final reaction mixture pH of about 12 to 13±0.2. The borate also acts as a pH buffer.

In modern automatic analyzers, reagents in substantial quantities are often stored on-board the equipment. Thus multiple samples can be analyzed before refilling is necessary. However, in clinical practice, many reagents are unstable at room temperatures, and require refrigeration. Therefore, certain modern automatic analyzers are equipped with refrigerated reagent chambers. Therein lies the problem solved by the present invention.

Because of the relatively labile nature of the picrate ion in alkaline conditions, generally a liquid creatinine reagent based on the Jaffe reaction comprises two components. The first component, a picric acid solution, comprises picric acid and deionized water. The second component, an alkaline buffer, can comprise sodium dodecyl sulfate and sodium tetraborate for reducing interference by proteins and carbohydrates, respectively, sodium phosphate as pH buffer, sodium hydroxide to provide alkalinity, polypropylene glycol for foam control, and deionized water. The dynamic range of a creatinine reagent system is generally defined as the sample creatinine concentration range within which linear extrapolation of results is acceptable. For a creatinine reagent system having a dynamic range of 0.3 to 25 mg/dl creatinine, the following reagent system can be used: (a) picric acid component: 50 mM picric acid; (b) alkaline buffer: pH 13.1. The components are mixed in a proportion of about 1:4 picric acid: alkaline buffer) to form an assay ready reagent. The sample and the assay ready reagent is mixed in a proportion of about 1:5 sample:assay ready reagent). For the purpose of facilitating discussion, similar concentrations, ranges, and proportions are used throughout this application.

However, it was found that the active ingredients in the two separate components can precipitate out of solution at low temperatures For example, for a picric acid solution with a picric acid concentration of 50 mM or more, crystal formation occurs around 10° C. As for the alkaline buffer, sodium dodecyl sulfate at a concentration of 1 5 wt. percent (in grams per deciliter) or more precipitates out at temperatures less than 18° C. Other solutes such as sodium phosphate and sodium tetraborate also precipitate at near freezing temperatures.

A major problem with such precipitates is that they can interfere with reagent metering in the automatic analyzer. The precipitates in worst cases can clog up the micropipets, and generally interfere with the accurate metering of the liquid components. Thus assay reproducibility becomes a problem. One solution to the problem is of course to equip the analyzer with multiple reagent chambers, some refrigerated and some maintained at room temperature. But this is not satisfactory, as it involves more complicated engineering and thus higher costs.

What is needed is a reagent for the determination of creatinine, having components which do not have precipitation problems at low temperatures.

SUMMARY

The present invention satisfies this need. It is related to a cold stable reagent system suitable for use in a Jaffe method for the determination of creatinine comprising:

(a) a homogeneous liquid picric acid component comprising picric acid in an amount of no more than about 40 mM, such that the picric acid component remains visibly homogeneous at a temperature as low as about 0° C. for about one year or more);

(b) a homogeneous liquid alkaline buffer component comprising:
(i) an alkaline material in sufficient amount to maintain the pH of the alkaline buffer component at more than about 13, for controlling the pH of the assay ready reagent formed by combining the picric acid and alkaline buffer components;
(ii) at least one pH buffer material
(iii) a detergent for reducing interference by proteins in the Jaffe method; and Wherein the alkaline buffer components contains substantially no metallic cations such that the component remains visibly homogeneous at a temperature as low as about 0° C. for about one year or more. Preferably the detergent is a soluble organic sulfate having a cationic portion and an anionic portion, the anionic portion being an organic sulfate having about 8 to about 12 carbons and the cationic portion being selected from the group consisting of diethanolamine, diethylamine, triethanolamine, and triethylamine; and wherein the alkaline material is selected from the group consisting of tetramethylammonium hydroxide, and tetramethanolammonium hydroxide. Preferably the alkaline buffer component further comprises about 1% (v/v) n-butanol, and polypropylene glycol in an amount between about 0 to about 2% (v/v).

Preferably the picric acid component comprises no more than about 35 mM acid. Preferably the alkaline buffer component also contains borate for reducing carbohydrates in the Jaffe method. Preferably both the picric acid component and the alkaline buffer component each remains visibly homogenous at least at a temperature between about 2° to about 8° C. for 30 days or more.

In a preferred version, the cold stable reagent system is suitable for use in a rate Jaffe method for the determination of creatinine in a sample having a creatinine concentration in the range of from about 0 3 to about 30 mg/dl, the reagent system comprising:

(a) a homogeneous liquid picric acid component consisting of about 35 mM of picric acid and deionized water, such that the picric acid component remains visibly homogeneous at a temperature between about 2° to about 8° C. for 30 days or more);

(b) a homogeneous liquid alkaline buffer component comprising:
(i) tetramethylammonium hydroxide in an amount between about 350 to about 550 mM
(ii) phosphoric acid as buffer, in an amount between about 25 to about 35 mM)
(iii) diethanolamine dodecyl sulfate in an amount between about 1.2 to about 1.5% (v/v) as detergent to reduce interference by proteins in the rate Jaffe method;
(iv) O-boric acid in an amount between about 40 to about 60 mM, to reduce interference by carbohydrates in the rate Jaffe method;
(v) about 1% (v/v) n-butanol; and
(vi) polypropylene glycol in an amount between about 0 to about 2% (v/v);

Wherein the alkaline buffer component contains substantially no metallic cation such that the component remains visibly homogeneous at a temperature between about 2° to about 8° C. for 30 days or more; and wherein an assay ready reagent formed by combining one part of the picric acid component and four parts of the alkaline buffer component has a pH of 13.1 or more.

DRAWINGS

These and other features, aspects, and advantages of the present invention will become better understood with reference to the following description, appended claims, and the accompanying drawings where:

DESCRIPTION

The creatinine reagent of the present invention has two homogeneous liquid components, namely a picric acid component and an alkaline buffer component. The invention is based on the discovery that the substantial elimination of metal ions from the alkaline buffer component renders the alkaline buffer component cold stable. Keeping the picric acid concentration in the picric acid component below about 40 mM also renders the picric acid component cold stable. Being "cold stable" is defined herein as remaining visibly homogeneous, i.e. as having no visible clouding or precipitate formation, at a temperature of 2°–8° C., for 30 days or more. Preferably the cold stable reagents stay visibly homogenous at a temperature down to about 0° C. for over one year or more.

For ease of discussion, the following description relates to a preferred version of the liquid creatinine reagent system of the present invention, in which the two components are designed to be mixed in a proportion of about 1:4 (picric acid: alkaline buffer) to form an assay ready reagent. The assay ready reagent is designed to be mixed with the sample in a proportion of about 5:1 (reagent:sample). The dynamic range of the reagent system (i.e. the sample creatinine concentration range within which linear extrapolation of results is acceptable) system is from about 0.3 to about 30 mg/dl. These numbers are for illustration purposes only, and are not meant to limit the scope of the present invention in any way.

The cold stable creatinine liquid reagent of the present invention comprises two homogeneous liquid components, namely a picric acid component and an alkaline buffer component.

The picric acid component comprises picric acid in an amount of no more than about 40 mM, more preferably no more than about 35 mM, and deionized water. This picric acid component remains visibly homogeneous at a temperature as low as 0° C. for about one year or more. Because lowering the picric acid concentration lowers the assay activity in a Jaffe reaction, it is preferred that the picric acid concentration be as high as possible without exceeding the above limit.

The alkaline buffer component comprises:
(a) an alkaline material in sufficient amount to maintain the pH of the alkaline buffer component at more than about 13, for controlling the pH of the assay ready reagent formed by combining the picric acid and alkaline buffer components;

(b) at least one pH buffer material; and (c) a detergent for reducing interference by proteins in the Jaffe method;

Wherein the alkaline buffer components contains substantially no metallic cations such that the component remains visibly homogeneous at a temperature as low as 0° C. for about one year or more.

Preferably the alkaline buffer component also contains borate for reducing interference by carbohydrates in the Jaffe method. Preferably the picric acid and alkaline buffer components each remains visibly homogenous at a temperature between about 2° to about 8° C. for 30 days or more.

In the prior art alkaline buffer component, the functional entities are mostly anionic in nature: the dodecyl sulfate and borate anions prevent protein and carbohydrate interference, the borate and phosphate buffer the pH, and hydroxyl ions from sodium hydroxide maintains the high pH. It was found that cold precipitation in the alkaline buffer component is a problem if the counter-ions (cations) are metal ions. The precipitation problem is pronounced even with the more soluble metallic species, such as lithium, sodium, potassium and magnesium. It was found that the substantial elimination of metal ions from the alkaline buffer component solves the low temperature precipitation problem. The task that remains is the selection of suitable counter-ions (cations). Criteria for the selection of counter-ions in the alkaline buffer component include: good solubility of the chemical species involved, little or no interference with the function of the anions availability and reasonable costs.

In the reagent system of the present invention, the detergent can be an organic sulfate detergent having about 8 to about 12 carbons. Examples include octosulfates, decyl sulfates, dodecyl sulfates, etc. Suitable counter-ions for the detergent sulfate include amines such as diethanolamine, triethanolamine, diethylamine, triethylamine, etc. Currently only di- and triethanolamine salts of dodecyl sulfate are readily available at reasonable costs. The other salts could be available through custom titration of the acid organic sulfates. The ammonium salts of organic sulfates are not acceptable because of pH and volatility considerations. Tetraalkylammonium salts of organic sulfates should be avoided, as high concentrations of tetra-alkylammonium ions can cause precipitation with picrate ions. A preferred detergent is diethanolamine dodecyl sulfate, because of cost and availability considerations. It should be noted that most commercially available versions of diethanolamine dodecyl sulfate contain small amounts of dodecanol and other high molecular weight aliphatic alcohols (C8-C13), which can cause cloudiness in the alkaline buffer component at temperatures less than about 20° C. To compensate, a low molecular weight linear alcohol, such as n-butanol, can be added to the alkaline buffer component to keep the high molecular weight alcohols in solution. It was found that n-butanol at a concentration of up to about 1% (v/v) does not interfere with rate Jaffe determinations.

The source of hydroxide for the alkaline buffer can be tetramethylammonium hydroxide (TMA—OH). Other high molecular weight tetra-alkylammonium hydroxides (e.g. tetra ethyl-, propyl-, butyl-, etc.) are unsatisfactory. They form precipitates with picrate almost instantaneously, and interfere with the creatinine assay.

Quaternary ammonium compounds have been used frequently in research either to purify polyanionic polysaccharides or to fractionate acidic polysaccharides from neutral polysaccharides by selective precipitation. It is also reported that quaternary ammonium cations can be precipitated quantitively with picric acid. It is surprising that tetramethylammonium hydroxide is suitable for providing the alkalinity needed in the alkaline buffer. Depending on the concentration of the species, tetramethylammonium ions (TMA+) will form precipitates with picrate ions, but it generally takes more than about fifteen minutes for the precipitates to become noticeable. This is well in excess of the three to ten minutes necessary to perform a rate Jaffe assay on an automatic analyzer. As precipitation of TMA-picrate speeds up with a higher TMA+ concentration, it is preferred that the TMA+ concentration be kept at a minimum in the alkaline buffer component. For a creatinine reagent system where the components are designed to be mixed in a proportion of about 1:4 (picric acid: alkaline buffer), where the picric acid concentration does not exceed about 35 mM in the picric acid component, the TMA+ conclusion in the alkaline buffer is preferably less than about 1,000 mM, more preferably less about than about 500 mM. Another suitable hydroxide source is tetraethanolammonium hydroxide, although it is more expensive than TMA-OH.

The pH buffer in the alkaline buffer component can be phosphate, added in the form of phosphoric acid. The pKa of a buffer is the pH where the buffering capacity is optimal. Usually buffers are used to maintain a pH of pKa ±1.0. Phosphate has 3 known pKa's. The pKa3 of phosphate is 12.3, making it suitable for buffering a pH of 13.1±0.2. An alternative organic buffer can be guadinine, which has a pKa higher than that of phosphate, and which is available as the *HCL or *HCO$_3$ salt.

The borate can be added as orthoboric acid. A small amount of polypropylene glycol can be added as a defoamer. The balance of the alkaline buffer component is deionized water.

Preferably the metal ions in the alkaline buffer constitutes no more than 10% of the total cations present, more preferably no more than 5%, and most preferably there is a substantial absence of all metal cations. Preferably the picric acid component also contains substantially no metal cations.

The components of the cold stable creatinine reagent should be stored at room temperature until they are needed on board the instrument. They can remain visibly homogeneous for at least 30 days at a temperature of 2°–8° C., more preferably for one year or more at a temperature as low as 0° C. Care should be taken so that the alkaline buffer and the TMA-OH raw material are not exposed to inordinately high temperatures for any period of time. Heat can cause the TMA+ to undergo a Hoffman rearrangement (demethylation) which results in trimethylamine and methanol. Therefore heat damage may cause pH changes in the alkaline buffer. Because TMA+ will react with picrate over time to form precipitates, it is preferred that the components of the cold stable creatinine reagent be mixed to form the assay ready reagent only shortly before the assay is performed. Stability of the assay ready reagent is projected to be between 3–7 days at room temperature.

In a less preferred version of the cold stable creatinine reagent of the present invention, where the picric acid component has a picric acid concentration of no more than about 35 mM, and the alkaline buffer component has a pH comparable to that of the prior art (about 13.1), the assay ready reagent can have a sensitivity 50% lower than that of the prior art formulation (when used on a COBAS-BIO from Roche Diagnostics of Nutley, N.Y., using a measurement window from 35 seconds to 45 seconds, with a window size of 10 seconds). Most of the decrease in sensitivity is due to the lower concentration of picrate. The amount of signal can be increased by at least 5–10% by moving up the measurement window from 35 seconds to 45 seconds, to from 25 seconds to 35 seconds or even from 15 seconds to 25 seconds, OR increasing the window size from 10 seconds to 20 or 30 seconds.

To compensate for the loss of sensitivity due to decrease in picrate concentration, it is necessary to increase the pH of the alkaline buffer component to increase the signal in the rate Jaffe assay. However, to keep the TMA+ concentration low to slow down TMA-picrate precipitate formation), the use of tetraethanolammonium hydroxide to increase the pH is preferred. If the pH is increased, a buffer with a pKa higher than phosphate, such as guadinine, should be used.

Alternatively, the pH of the alkaline buffer can be adjusted upwards, e.g. to about 13.35 to about 13.55, without increasing the amount of TMA-OH, by reducing the amounts of phosphate and borate buffer. This latter method of pH adjustment is more preferred. At these higher pH levels, the cold stable creatinine reagent of this invention, using a 35 mM picric acid component, can have sensitivities comparable to that of the prior art reagent using a 50 mM picric acid component. The examples that follow demonstrate such results.

The advantages afforded by the cold stable creatinine reagent of the present invention are many. The chemical solutes in the components can remain dissolved in the aqueous phase at a temperature as low as 0° C. This allows the components to be stored on-board clinical analyzers that require reagent refrigeration because of engineering design considerations. Freeze-thaw recoverability is also less of a concern e.g., with respect to shipping during the winter months. The alkaline buffer is resistant to freeze/thaw damage, as demonstrated by the absence of cloudiness in the alkaline buffer after thawing. This allows the alkaline buffer to be used immediately after thawing.

EXAMPLES

In the following examples, it is shown that the sensitivity of the cold stable creatinine reagent of the present invention compares favorably in most respect with prior art creatinine reagents. All rate Jaffe determinations were measured as two-point rate on a COBAS-BIO (Roche Diagnostics of Nutley, N.J.). Below is a listing of the COBAS-BIO parameters:

| 1.  | UNITS                     | MG/DL |
|-----|---------------------------|-------|
| 2.  | CALCULATION FACTOR        | 0     |
| 3.  | STANDARD 1 CONC           | 5     |
| 4.  | STANDARD 2 CONC           | 5     |
| 5.  | STANDARD 3 CONC           | 5     |
| 6.  | LIMIT                     | 25    |
| 7.  | TEMPERATURE [DEG. C.]     | 37    |
| 8.  | TYPE OF ANALYSIS          | 4     |
| 9.  | WAVELENGTH [NM]           | 520   |
| 10. | SAMPLE VOLUME [mL]        | 25    |
| 11. | DILUENT VOLUME [mL]       | 25    |
| 12. | REAGENT VOLUME [mL]       | 250   |
| 13. | INCUBATION TIME [SEC]     | 180   |
| 14. | START REAGENT VOLUME [mL] | 0     |
| 15. | TIME OF FIRST READING [SEC] | 25  |
| 16. | TIME INTERVAL [SEC]       | 10    |
| 17. | NUMBER OF READINGS        | 2     |
| 18. | BLANKING MODE             | 0     |
| 19. | PRINTOUT MODE             | 4     |

REAGENT SOURCE

Diethanolamine Dodecyl Sulfate (33–35%) is available from Pfaltz & Bauer, Waterbury, Conn.; Tetramethylammonium Hydroxide (25%) is available from Southwestern Analytical Chemicals, Austin, Tex.

The other reagents used are standard off-the-shelf items. The only requirement is that they be of good quality and purity (e.g., ACS grade).

The following reagents were tested:

| A. PRIOR ART REAGENT (PA) | |
|---|---|
| 1. Picric Acid Component | |
| (a) 50 mM picric acid | |
| (b) deionized water (NCCLS class II) | |
| 2. Alkaline Buffer Component | |
| (a) Sodium Dodecyl Sulfate | 1.5 wt. % (grams/dl) |
| (b) Sodium Tetraborate Decahydrate | 100 mM as borate |
| (c) Sodium Phosphate (tribasic) | 62 mM |
| (d) Sodium Hydroxide | 187.5 mM |
| (e) Polypropylene Glycol 1025 | 0.2% (v/v) |
| (f) Deionized water (NCCLS Class II) makes up the balance. | |
| (g) pH | 13.1 |
| B. COLD STABLE REAGENTS (CS) | |
| 1. Picric Acid Component | |
| (a) 35 mM picric acid | |
| (b) deionized water (NCCLS Class II) | |
| 2. Alkaline Buffer Component | |

| | SAMPLES | | | |
|---|---|---|---|---|
| | CS1 | CS2 | CS3 | CS4 |
| (a) Diethanolamine Dodecyl Sulfate | 1.35% | 1.35% | 1.35% | 1.35% |
| (b) O-Boric Acid (measured as borate) | 100 mM | 50 mM | 50 mM | 50 mM |
| (c) 85% Phosphoric Acid | 62 mM | 31.3 mM | 31.3 mM | 31.3 mM |
| (d) TMA-OH | 420 mM | 390 mM | 450 mM | 510 mM |
| (e) Polypropylene Glycol 1025 (v/v) | 0.2% | 0.2% | 0.2% | 0.2% |

| -continued | | | | |
|---|---|---|---|---|
| (f) pH | 13.1 | 13.35 | 13.45 | 13.55 |

*Deionized water (NCCLS Class II) makes up the balance.

The picric acid component and the alkaline buffer component in each reagent were mixed in a ratio of 1:4 (picric acid: alkaline buffer) to form the assay-ready reagent before the assay is performed.

EXAMPLE 1

The activities of the CS1 reagent were compared to that of the PA reagent, using a 10 mg/dl aqueous creatinine standard. The results are tabulated in Table 1. The results show that because of the lower picrate concentration (35 mM vs 50 mM), the activity of the CS1 reagent can be less than half of that of the prior art reagent.

TABLE 1
SENSITIVITY EVALUATION
PRIOR ART VS COLD STABLE REAGENTS
10.0 MG/DL AQUEOUS CREATININE STANDARD
25-35 SEC WINDOW
VALUES IN dA/MIN

| | PA | CS1 |
|---|---|---|
| | 0.2464 | 0.1249 |
| | 0.2429 | 0.1184 |
| | 0.2385 | 0.1147 |
| | 0.2368 | 0.1121 |
| | 0.2486 | 0.1182 |
| | 0.2453 | 0.1152 |
| | 0.2505 | 0.1132 |
| | 0.2465 | 0.1174 |
| | 0.2472 | 0.1191 |
| | 0.2467 | 0.1165 |
| | 0.2488 | 0.1215 |
| | 0.2465 | 0.1164 |
| | 0.2494 | 0.1160 |
| | 0.2462 | 0.1203 |
| | 0.2513 | 0.1181 |
| | 0.2472 | 0.1198 |
| | 0.2481 | 0.1198 |
| | 0.2488 | 0.1178 |
| | 0.2501 | 0.1212 |
| | 0.2477 | 0.1206 |
| | 0.2513 | 0.1190 |
| | 0.2467 | 0.1146 |
| | 0.2455 | 0.1191 |
| | 0.2425 | 0.1182 |
| | 0.2469 | 0.1198 |
| AVG. | 0.2467 | 0.1181 |
| S.D. | 0.0034 | 0.0028 |
| % CV | 1.39 | 2.35 |

(%CV = % Coefficient of Variation = $\frac{S.D}{AVG.} \times 100\%$)

EXAMPLE 2

The alkaline buffer components in reagents CS2, CS3, and CS4 were formulated with the goal of increasing the hydroxide concentration without elevating the TMA+ concentration to a level where the formation of TMA-picrate complex is favorable. The borate and phosphate concentrations were reduced by 50% as compared to both reagents PA and CS1. It was found that higher pHs can then be obtained without significantly elevating the TMA+ concentration. Using a 10 mg/dl aqueous creatinine standard, cold stable reagents CS2, CS3, and CS4 were compared against the prior art reagent PA, in terms of sensitivity, linearity of results, within-run precision, correlation with the prior art reagent, and resistance to drug interferences. It was found that these novel cold stable creatinine reagents exhibit excellent performance on the COBAS BIO.

A. Sensitivity

The rate signals obtainable with the new high-pH cold stable formulations are found to be comparable to that of the prior art reagent. Table 2 tabulates the results of such a comparison.

TABLE 2
SENSITIVITY OF NEW
COLD STABLE ALKALINE BUFFER
FORMULATION VS THAT OF PRIOR ART REAGENT
ASSAY READY MIXTURE
PA: 4 parts (v/v) alkaline buffer to 1 part 50 mM picric acid.
CS: 4 parts (v/v) alkaline buffer to 1 part 35 mM picric acid.
10.0 MG/DL AQUEOUS STANDARD
25-35 SEC WINDOW
VALUES IN dA/MIN

| Alkaline Buffer | PA pH 13.1 | CS2 pH 13.35 | CS3 pH 13.45 | CS4 pH 13.55 |
|---|---|---|---|---|
| | 0.2180 | 0.2001 | 0.2340 | 0.2499 |
| | 0.2186 | 0.1984 | 0.2387 | 0.2474 |
| | 0.2189 | 0.2031 | 0.2407 | 0.2518 |
| | 0.2251 | 0.2000 | 0.2406 | 0.2512 |
| | 0.2248 | 0.2027 | 0.2407 | 0.2549 |
| | 0.2278 | 0.2011 | 0.2427 | 0.2526 |
| | 0.2278 | 0.2016 | 0.2431 | 0.2514 |
| | 0.2211 | 0.2013 | 0.2398 | 0.2521 |
| | 0.2208 | 0.2030 | 0.2458 | 0.2554 |
| | 0.2219 | 0.2030 | 0.2422 | 0.2526 |
| | 0.2220 | 0.2019 | 0.2406 | 0.2557 |
| | 0.2234 | 0.2032 | 0.2437 | 0.2548 |
| | 0.2219 | 0.2046 | 0.2434 | 0.2559 |
| AVG | 0.22 | 0.20 | 0.24 | 0.25 |
| SD | 3.33E-03 | 1.48E-03 | 3.08E-03 | 2.28E-03 |
| % CV | 1.49 | 0.73 | 1.28 | 0.90 |

It was found that the sensitivity, in dA/min., of the preferred version of the new cold stable formulation reagents can compare favorably with that of the prior art reagent, if the alkaline buffer has a pH of about 13.35 or greater.

B. Linearity of Results

Figure 1:
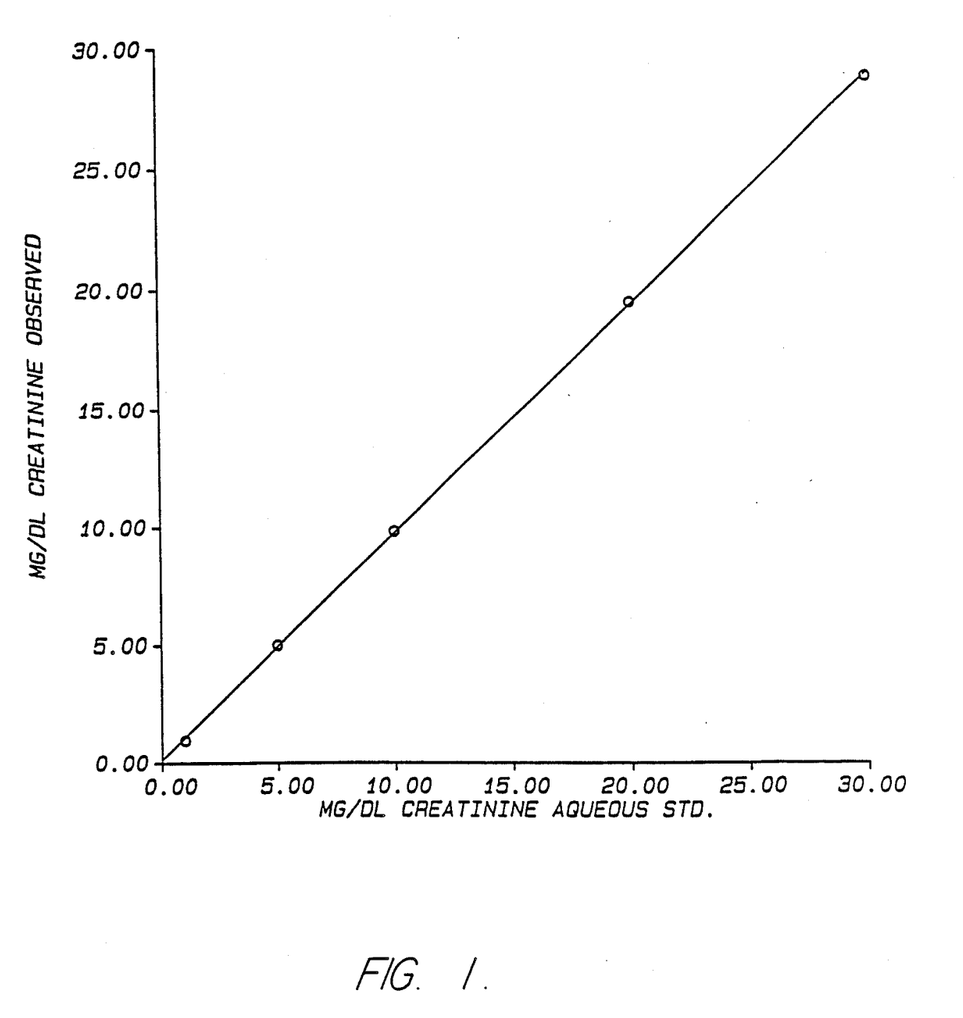
FIG. 1 is a plot of the linearity range of a preferred version of a cold stable creatinine reagent according to the present invention.
Figure 2:
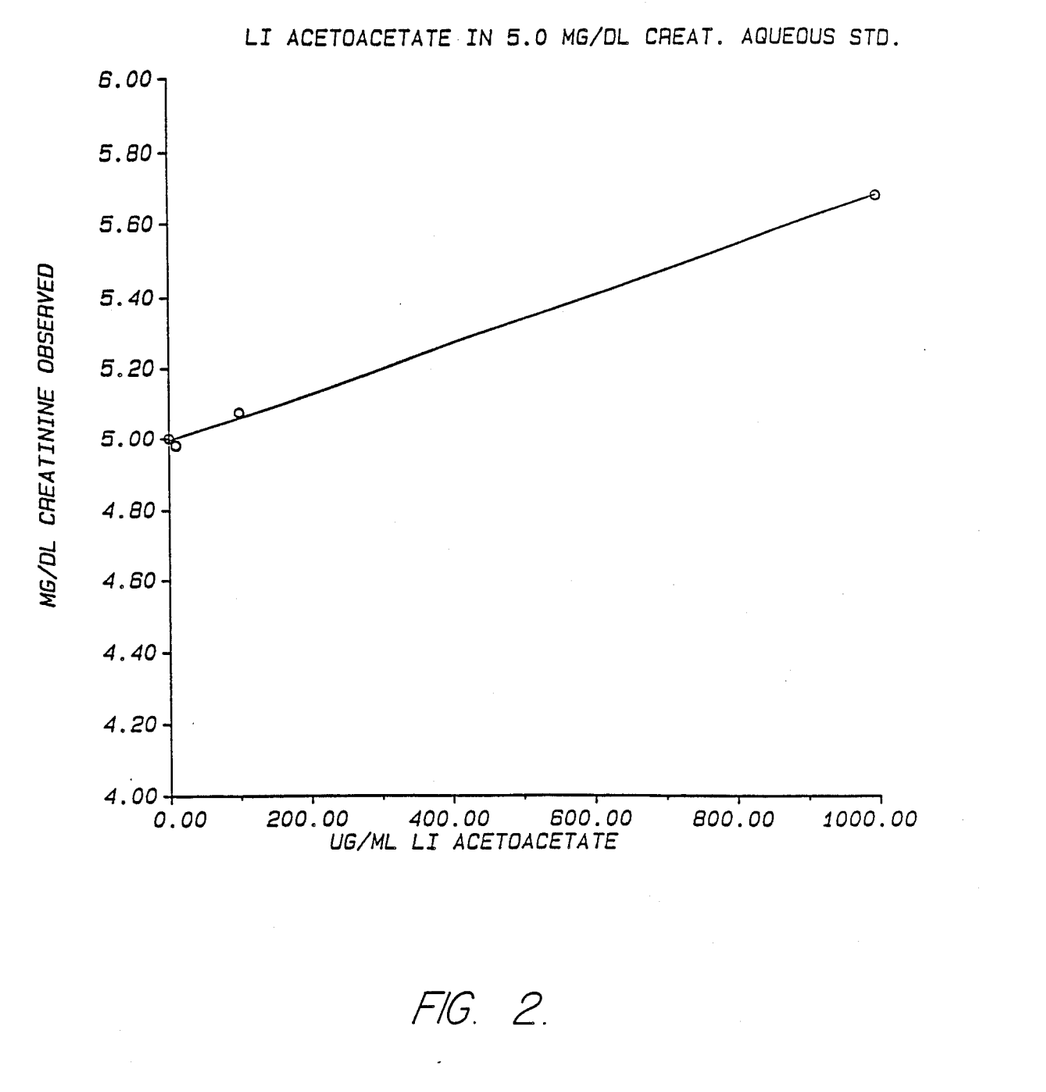
FIGS. 2–5 are plots showing the interference effects of lithium acetoacetate and cephalothin on a preferred version of a cold stable creatinine reagent of the present invention.
Figure 3:
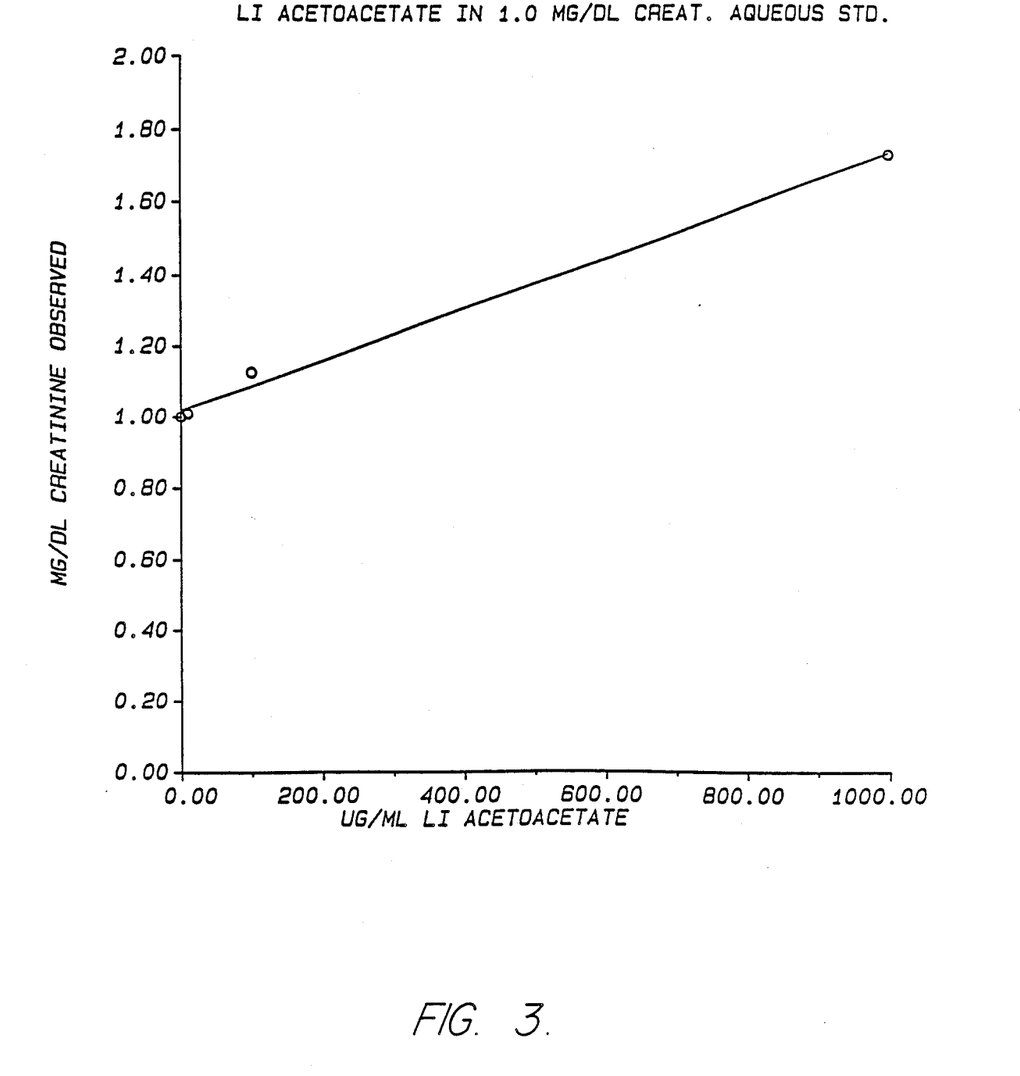
Figure 4:
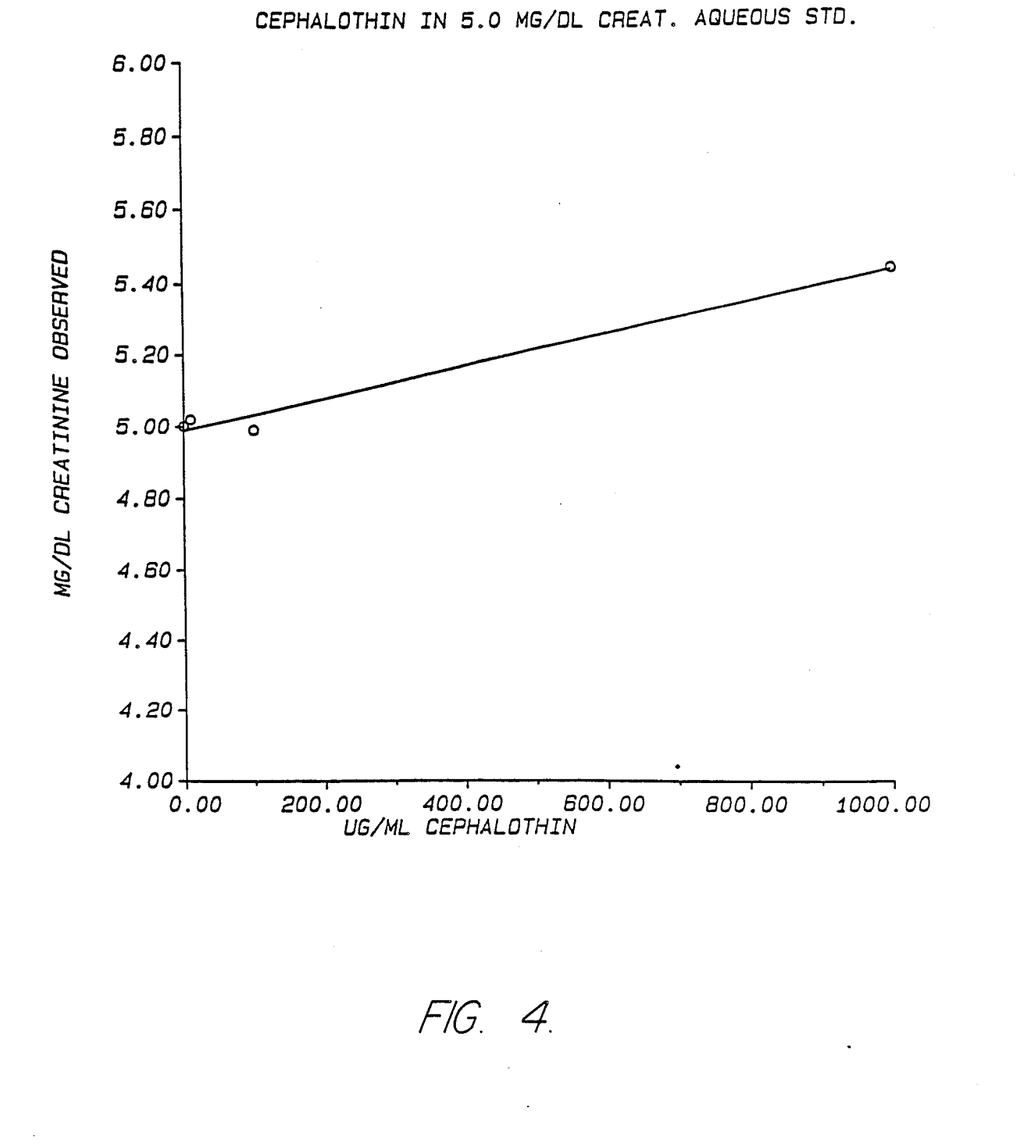
Figure 5:
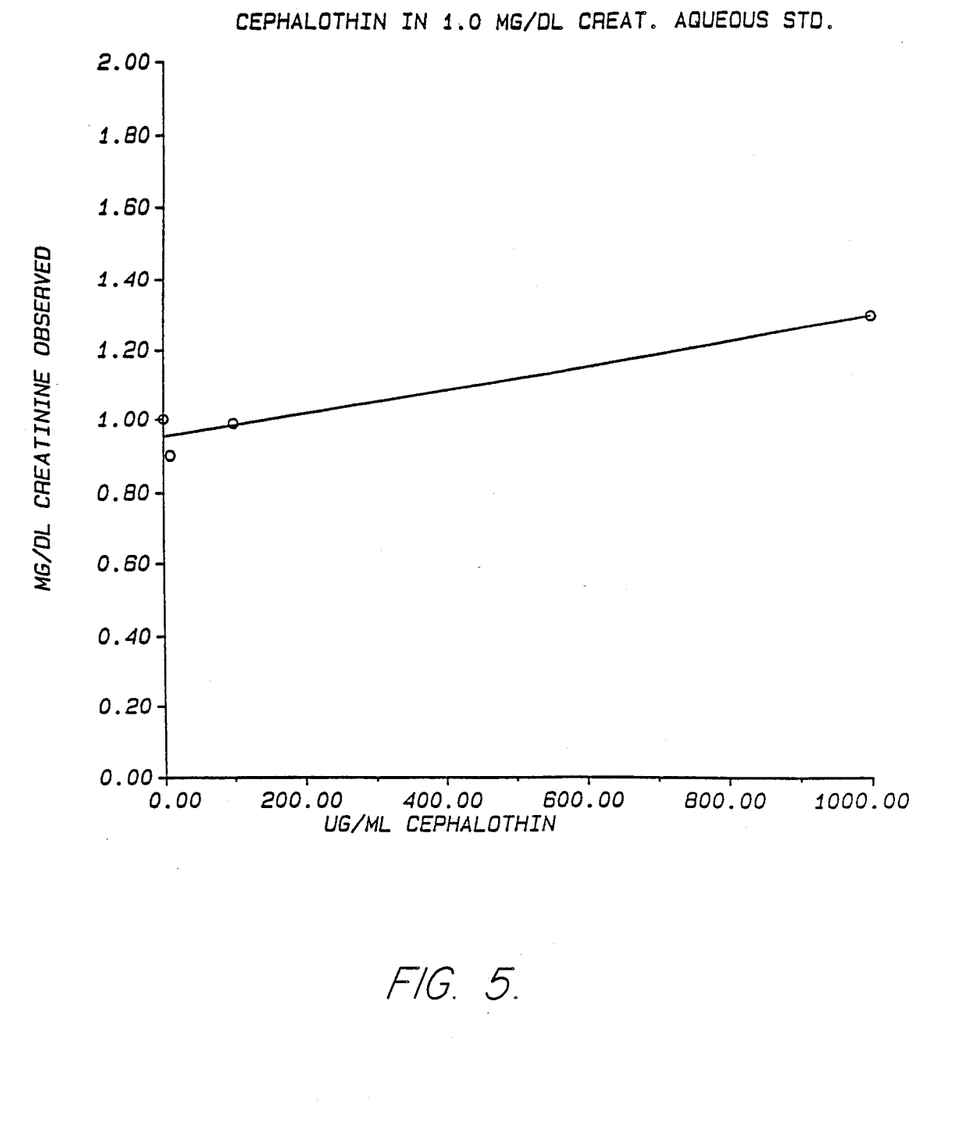
Figure 6:
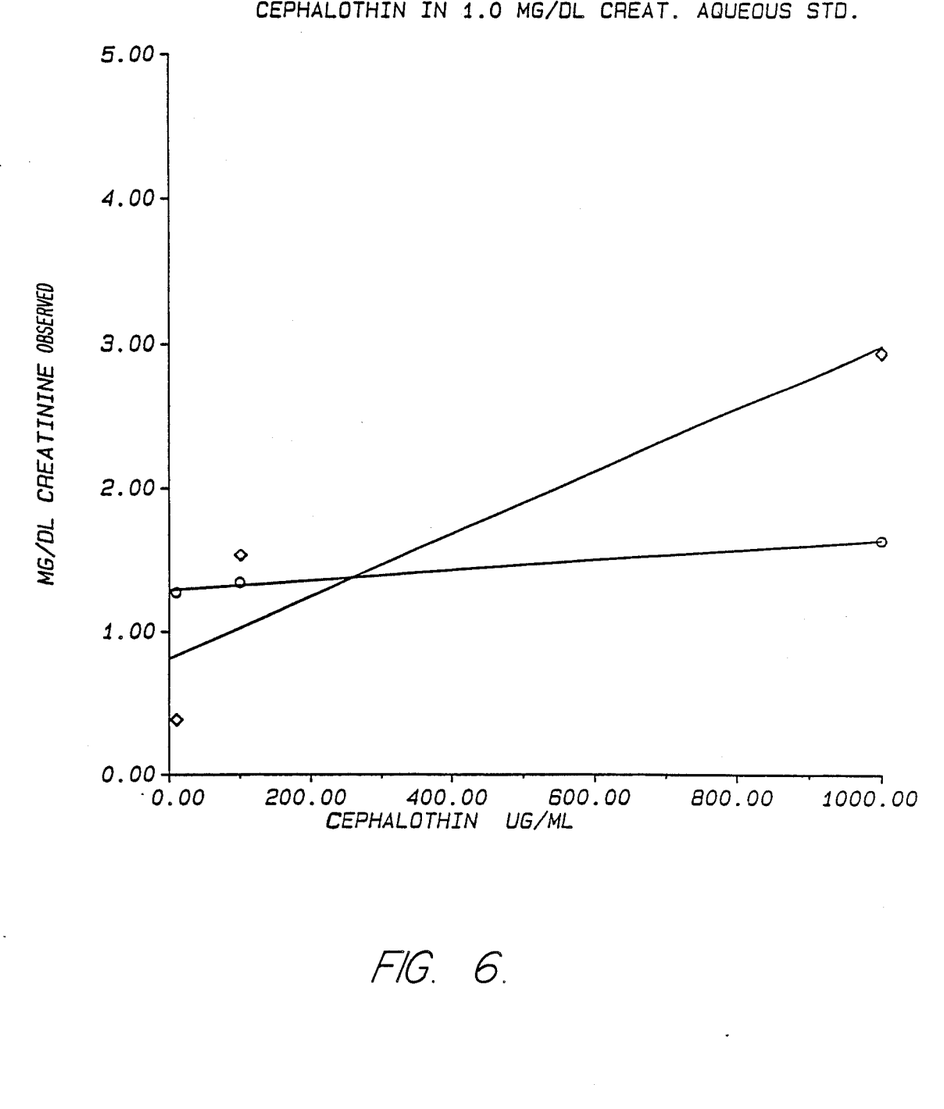
FIGS. 6–9 are plots comparing the interference effects of lithium acetoacetate and cephalothin on (a) a prior art creatinine reagent, and (b) a preferred version of the cold stable creatinine reagent of the present invention.
Figure 7:
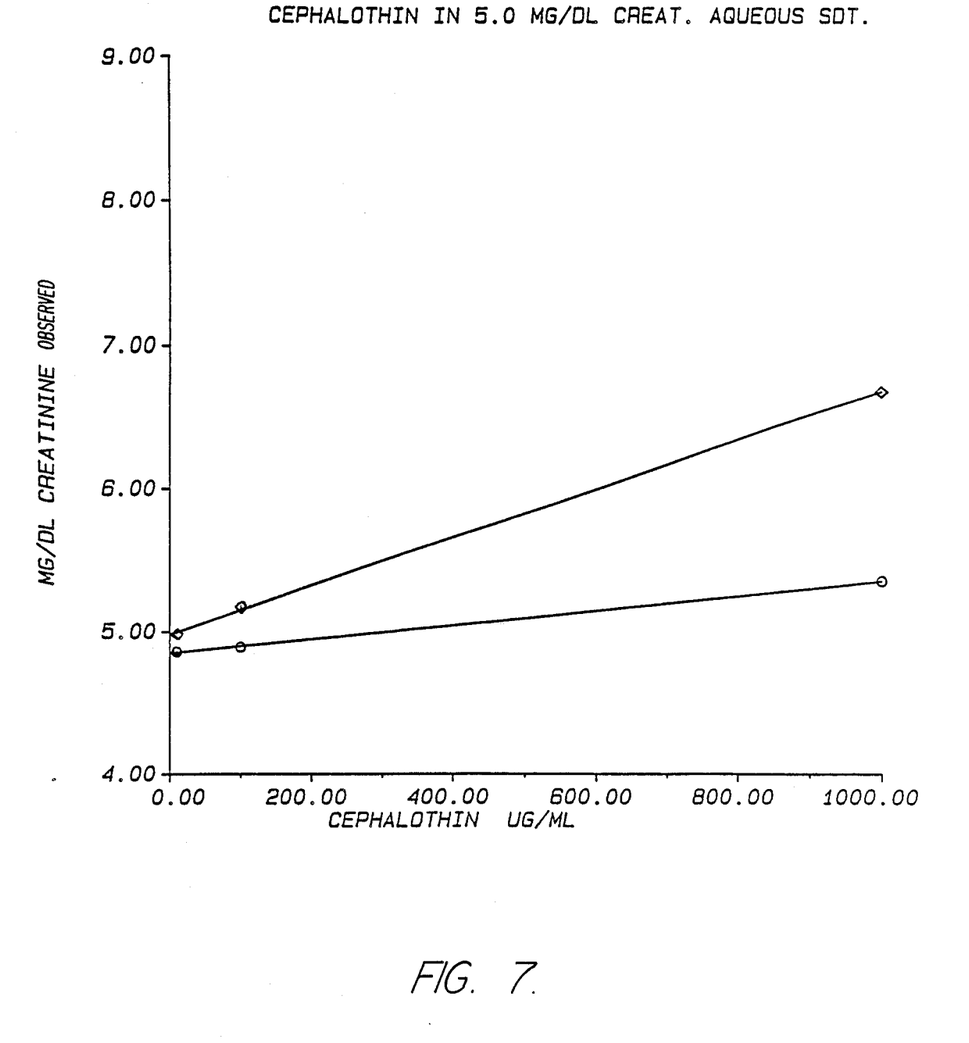
Figure 8:
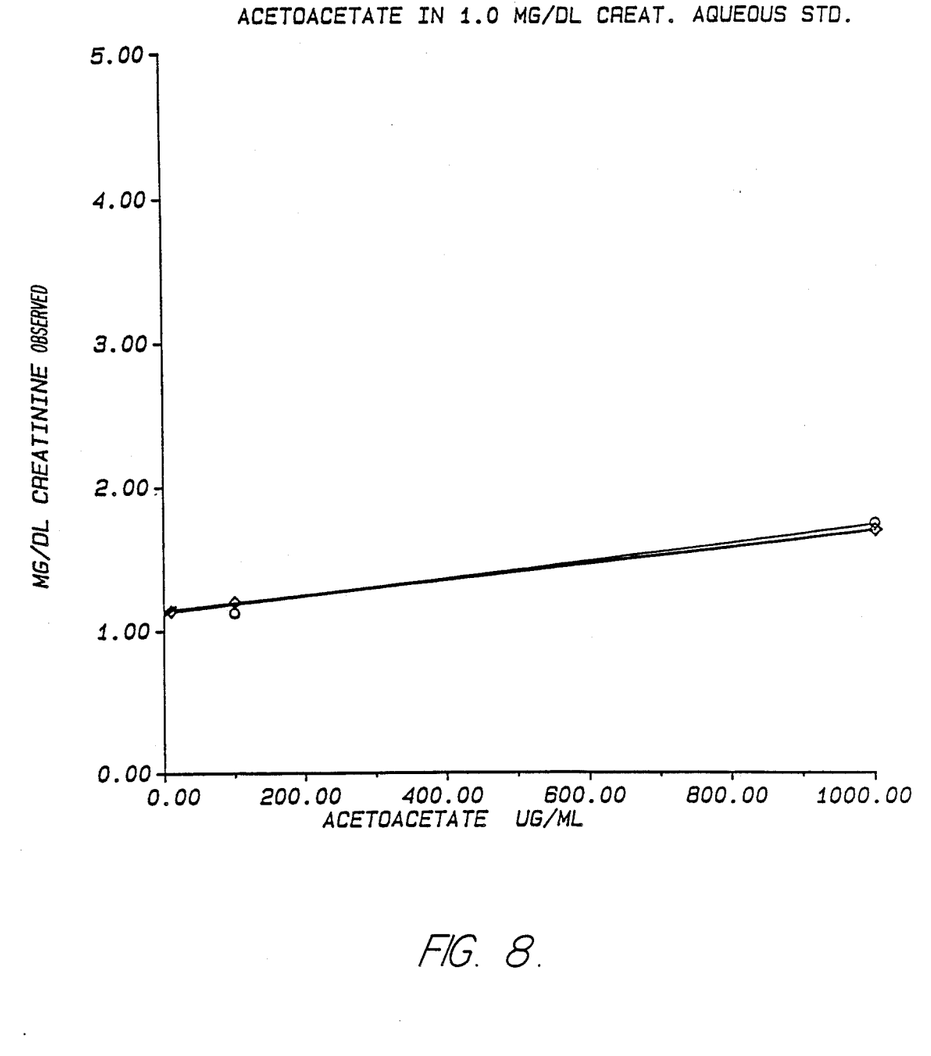
Figure 9:
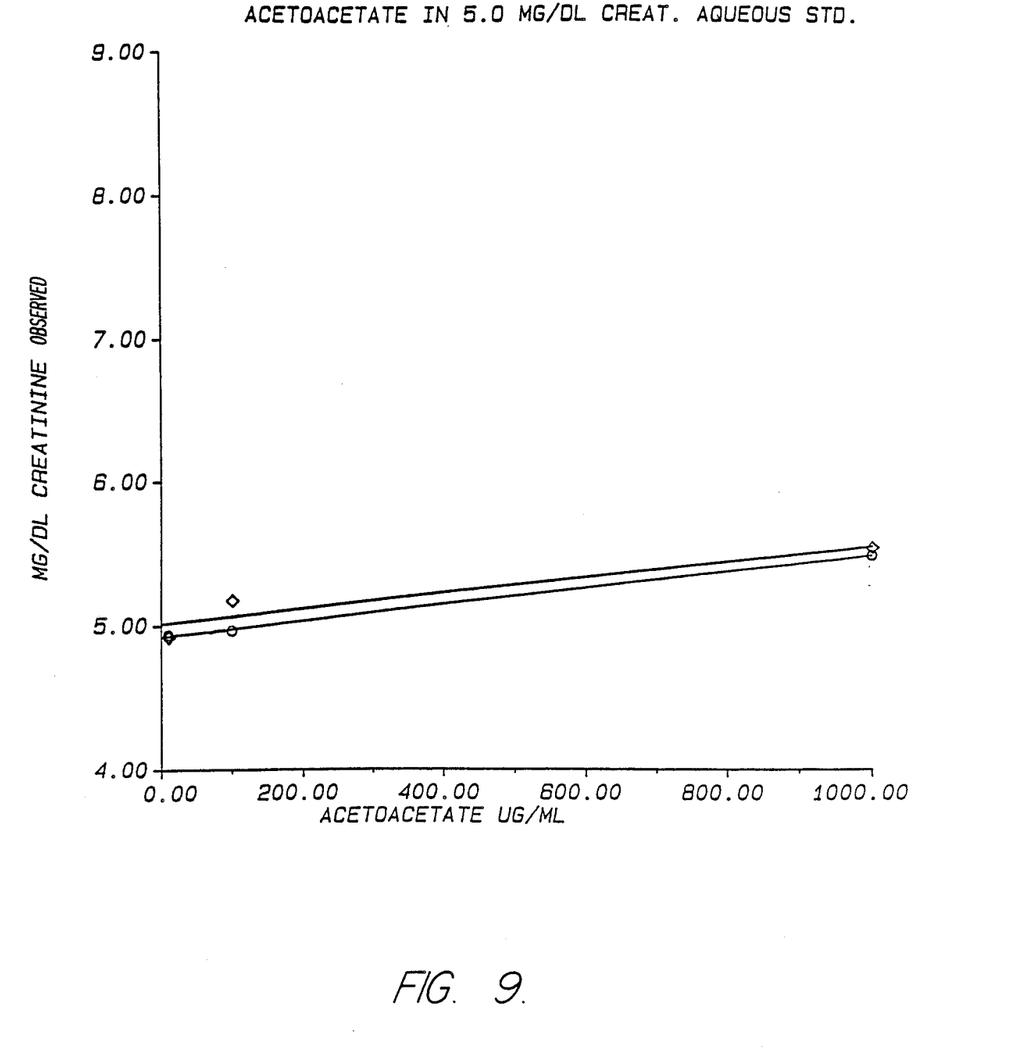

The linearity of results within the dynamic range of the new CS-3 formulation reagent was studied, using the COBAS-BIO procedure described above. FIG. 1 is a summary of the test results. Excellent linearity within a dynamic range of 0.3 mg/dL to 30 mg/dL, was observed with a correlation coefficient of 0.9999.

C. Within Run Precision

Three Beckman ™ human serum based samples were run in parallel, using the CS3 reagent (13.45 pH). The runs were repeated 24 times for each sample. The results are tabulated in Table 3.

TABLE 3
WITHIN RUN PRECISION STUDY
WITH HUMAN SERUM BASED SAMPLES
NEW COLD STABLE REAGENT (CS-3)

| Sample 1 mg/dl | Sample 2 mg/dl | Sample 3 mg/dl |
|---|---|---|
| 0.88 | 1.66 | 3.86 |
| 0.81 | 1.65 | 3.87 |
| 0.86 | 1.58 | 3.88 |
| 0.91 | 1.56 | 3.76 |

TABLE 3-continued
WITHIN RUN PRECISION STUDY WITH HUMAN SERUM BASED SAMPLES NEW COLD STABLE REAGENT (CS-3)

|  | Sample 1 mg/dl | Sample 2 mg/dl | Sample 3 mg/dl |
|---|---|---|---|
|  | 0.84 | 1.62 | 3.94 |
|  | 0.89 | 1.48 | 3.85 |
|  | 0.94 | 1.52 | 3.84 |
|  | 0.84 | 1.62 | 3.90 |
|  | 0.82 | 1.54 | 3.85 |
|  | 0.84 | 1.63 | 3.93 |
|  | 0.77 | 1.51 | 3.96 |
|  | 0.86 | 1.54 | 3.89 |
|  | 0.86 | 1.60 | 3.89 |
|  | 0.88 | 1.56 | 3.94 |
|  | 0.89 | 1.45 | 3.79 |
|  | 0.86 | 1.64 | 3.84 |
|  | 0.87 | 1 52 | 3.68 |
|  | 0.91 | 1.68 | 3.83 |
|  | 0.82 | 1.62 | 3.85 |
|  | 0.85 | 1.63 | 3.94 |
|  | 0.84 | 1 59 | 3.90 |
|  | 0.88 | 1.59 | 3.86 |
|  | 0.91 | 1.55 | 3.84 |
|  | 0.86 | 1.61 | 3.82 |
| AVG. | 0.86 | 1.59 | 3.86 |
| S.D. | 0.04 | 0.06 | 0.06 |
| % C.V. | 4.24 | 3.64 | 1.58 |

It is generally preferred that the within run precision meet a 2.0 mg/dl S.D. or a 3.0% C.V. requirement, whichever is greater. Thus the Cold Stable creatinine reagent of the present invention meets the requirements.

D. Correlation With Prior Art Reagent

Twenty-two (22) different samples were run on the COBAS BIO, using both the CS3 reagent and the PA reagent, to test the correlation of results using the new and old reagents. The results are tabulated in Table 4.

TABLE 4
CORRELATION NEW COLD STABLE REAGENT VS. PA REAGENT

|  | COBAS C.S.3 pH 13.45 | PA |
|---|---|---|
| AQUEOUS STD 1.0 mg/dl | 1.08 | 1.03 |
| AQUEOUS STD 5.0 mg/dl | 5.01 | 5.03 |
| AQUEOUS STD 10.0 mg/dl | 9.82 | 10.05 |
| AQUEOUS STD 20.0 mg/dl | 19.60 | 19.74 |
| AQUEOUS STD 30.0 mg/dl | 28.96 | 29.23 |
| BECKMAN ASTRA CALIBRATOR #1 | 0.98 | 1.07 |
| BECKMAN ASTRA CALIBRATOR #2 | 4.48 | 4.41 |
| STD CREAT. |  |  |
| 10 ug/ml LI ACETOACETATE | 1.19 | 1.14 |
| 100 ug/ml LI ACETOACETATE | 1.13 | 1.20 |
| 1000 ug/ml LI ACETOACETATE | 1.74 | 1.69 |
| STD CREAT. |  |  |
| 10 ug/ml LI ACETOACETATE | 4.94 | 4.92 |
| 100 ug/ml LI ACETOACETATE | 4.97 | 5.17 |
| 1000 ug/ml LI ACETOACETATE | 5.48 | 5.53 |
| STD CREAT. |  |  |
| 10 ug/ml CEPHALOTHIN | 1.27 | 0.38 |
| 100 ug/ml CEPHALOTHIN | 1.34 | 1.53 |
| 1000 ug/ml CEPHALOTHIN | 1.63 | 2.94 |
| STD CREAT. |  |  |
| 10 ug/ml CEPHALOTHIN | 4.86 | 4.98 |
| 100 ug/ml CEPHALOTHIN | 4.89 | 5.17 |
| 1000 ug/ml CEPHALOTHIN | 5.34 | 6.67 |
| DECISION #1 (human serum based sample) | 0.86 | 0.70 |
| DECISION #2 (human serum based sample) | 1.59 | 1.17 |
| DECISION #3 (human serum based sample) | 3.99 | 3.91 |

The results indicate no significant difference between the performance of the two reagents on the COBAS BIO, even in the presence of various interfering drugs.

E. Resistance to Drug Interferences

Drug interferences pose a major problem with the rate-Jaffe reaction. Cephalosporin and ketone bodies frequently pose positive interference problems. The interference effect of cephalothin (cephalosporins) and Li-acetoacetate (ketone bodies) on the CS-3 reagent was studied. The results are shown in Figures 2-5. They show that the CS reagent does not show dramatic positive interferences.

The effect of the above drugs on the CS-3 and prior art reagents were also then compared The results are summarized in FIGS. 6-9. The results show that the CS formulation performed at least as well or better than the prior art formulation with respect to resistance to drug interference.

Although the present invention has been described in considerable detail with reference to certain preferred versions thereof, other versions are possible. Therefore, the spirit and scope of the appended claims should not be limited to the description of the preferred versions contained herein.

What is claimed is:

1. A cold stable liquid reagent system suitable for use in a Jaffe method for the determination of creatinine comprising:
   (a) a homogeneous liquid picric acid component comprising picric acid in an amount of no more than about 40 mM, such that the picric acid component remains visibly homogeneous at a temperature as low as about 0° C. up to one year or more
   (b) a homogeneous liquid alkaline buffer component comprising:
      (i) an alkaline material in sufficient amount to maintain the pH of the alkaline buffer component at more than about 13, for controlling the pH of the assay ready reagent formed by combining the picric acid and alkaline buffer components;
      (ii) at least one pH buffer material; and
      (iii) a detergent for reducing interference by proteins in the Jaffe method;
   wherein the alkaline buffer components contain substantially no metallic cations such that the component remains visibly homogeneous at a temperature as low as about 0° C. up to 1 year or more.

2. The reagent system of claim 1 wherein the amount of metal cations comprise less than about 10% of the total amount of all cationic species in the alkaline buffer component.

3. The reagent system of claim 1 wherein the amount of metal cations comprise less than about 5% of the total amount of all cationic species in the alkaline buffer component.

4. The reagent system of claim 1 wherein the picric acid component also contains substantially no metallic cations.

5. The reagent system of claim 1 wherein the alkaline buffer component also comprises borate for reducing interference by carbohydrates in the Jaffe method.

6. The reagent system of claim 5 wherein the detergent is a soluble organic sulfate having a cationic portion and an anionic portion, the anionic portion being an organic sulfate having about 8 to about 12 carbons, and the cationic portion being selected from the group consisting of diethanolamine, diethylamine, triethanolamine, and triethylamine; and wherein the alkaline material is selected from the group consisting of tetramethylammonium hydroxide, and tetraethanolammonium hydroxide.

7. The reagent systems of claim 6 wherein the detergent is diethanolamine dodecyl sulfate, and the alkaline material is tetramethylammonium hydroxide.

8. The reagent system of claim 7 wherein the alkaline buffer component comprises:
   (a) tetramethylammonium hydroxide in an amount between about 350 to about 550 mM;
   (b) phosphoric acid as the buffer material, in an amount between about 25 to about 35 mM;
   (c) diethanolamine dodecyl sulfate as the detergent, in an amount between about 1.2 to about 1.5% (v/v); and
   (d) O-boric acid as the source of borate, in an amount between about 40 to about 60 mM;
   wherein the pH of the alkaline buffer component is between about 13.3 to about 13.6.

9. The reagent system of claim 8 wherein the picric acid component comprises 35 mM of picric acid, and the alkaline buffer component further comprises:
   (a) about 1% (v/v) n-butanol; and
   (b) polypropylene glycol in an amount between about 0 to about 2% (v/v).

10. A cold stable liquid reagent system suitable for use in a rate Jaffe method for the determination of creatinine in a sample having a creatinine concentration in the range of from about 0.3 to about 30 mg/dl, the reagent system comprising:
   (a) a homogeneous liquid picric acid component consisting of about 35 mM of picric acid and deionized water, such that the picric acid component remains visibly homogeneous at a temperature between about 2° to about 8° C. for 30 days or more;
   (b) a homogeneous liquid alkaline buffer component comprising:
      (i) tetramethylammonium hydroxide in an amount between about 350 to about 550 mM;
      (ii) phosphoric acid as buffer, in an amount between about 25 to about 35 mM;
      (iii) diethanolamine dodecyl sulfate in an amount between about 1.2 to about 1 5% (v/v) as detergent to reduce interference by proteins in the rate Jaffe method;
      (iv) O-boric acid in an amount between about 40 to about 60 mM, to reduce interference by carbohydrates in the rate Jaffe method;
      (v) about 1% (v/v) n-butanol, and
      (vi) polypropylene glycol in an amount between about 0 to about 2% (v/v);
   wherein the alkaline buffer component contains substantially no metallic cation such that the component remains visibly homogeneous at a temperature between about 2° to about 8° C. for 30 days or more and wherein an assay ready reagent formed by combining one part of the picric acid component and four parts of the alkaline buffer component has a pH of 13.0 or more.

* * * * *

REEXAMINATION CERTIFICATE (1780th)

United States Patent [19]

Seaton

[11] B1 4,950,611

[45] Certificate Issued  Aug. 25, 1992

[54] COLD STABLE LIQUID CREATININE REAGENT

[75] Inventor: Charles B. Seaton, San Diego, Calif.

[73] Assignee: Beckman Instruments, Inc.

Reexamination Request:
No. 90/002,545, Dec. 13, 1991

Reexamination Certificate for:
Patent No.: 4,950,611
Issued: Aug. 21, 1990
Appl. No.: 67,365
Filed: Jun. 26, 1987

[51] Int. Cl.$^5$ .............................................. G01N 33/70
[52] U.S. Cl. ..................... 436/98; 436/171; 436/175; 436/176
[58] Field of Search ..................... 436/8, 98, 171, 175, 436/176

[56] References Cited

PUBLICATIONS

"ASTRA System Creative Reagent Kit" Beckman Product Bulletin No. 668306.
Bowers, L. D. and Wong, E. T. "Kinetic Serum Creatine Assays. II. A Critical Evalution and Review." Clin. Chem. 26/5:555–561 (1980).
Vasiliades, J. "Reaction of Alkaline Sodium Picrate with Creatinine: I. Kinetics and Mechanism Formation of Mono–Creatinine Picric Acid Complex." Clin. Chem. 22/10:1664–1671, 1976.
Hyneck, M., et al., "Interference of Cephalosporins and Cefoxitin with Serum Creatinine Determination." Am. J. Hosp. Pharm. 38:1348–1352, 1981.
Slonecker, H., et al. "Spectrophotometric Determination of High Molecular Weight Quaternary Ammonium Cations with Picric Acid." Anal. Chem. 37/2, pp. 243–246, 1965.
Heinegard, D. and Tiderström, G. "Determination of Serum Creatinine by a Direct Colorimetric Method." Clinica Chimica Acta 43:305–310, 1973.
Bowers, L. D. "Kinetic Serum Creatinine Assays. I. The Role of Various Factors in Determining Specificity." Clin. Chem. 26/5:551–554, 1980.

*Primary Examiner*—James C. Housel

[57] ABSTRACT

A cold stable liquid reagent suitable for use in a Jaffe method for the determination of creatinine comprises:
(a) a homogeneous liquid picric acid component comprising picric acid in an amount of no more than about 35 mM, such that the picric acid component remains visibly homogeneous at a temperature between about 2° to about 8° C. for 30 days or more;
(b) a homogeneous liquid alkaline buffer component comprising:
 (i) an alkaline material in sufficient amount to maintain the pH of the alkaline buffer component at more than about 13, for controlling the pH of the assay ready reagent formed by combining the picric acid and alkaline buffer components;
 (ii) at least one pH buffer material;
 (iii) a detergent for reducing interference by proteins in the Jaffe method; and
 (iv) borate for reducing interference by carbohydrates in the Jaffe method;

wherein the alkaline buffer components contains substantially no metallic cations such that the component remains visibly homogeneous at a temperature between about 2° to about 8° C. for 30 days or more. Preferably the alkaline material is tetramethylammonium hydroxide, and the detergent is diethanolamine dodecyl sulfate.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-10 is confirmed.

* * * * *